United States Patent [19]

Kopacz

[11] Patent Number: 4,617,738
[45] Date of Patent: Oct. 21, 1986

[54] SURGICAL BLADE HANDLE

[75] Inventor: Bernard F. Kopacz, Little Falls, N.J.

[73] Assignee: Becton, Dickinson and Company, Franklin Lakes, N.J.

[21] Appl. No.: 603,856

[22] Filed: Apr. 25, 1984

[51] Int. Cl.⁴ .............................................. A61B 17/36
[52] U.S. Cl. ........................................ 30/339; 128/305
[58] Field of Search ....................... 128/305, 304, 751; 30/339, 338, 337

[56] References Cited

U.S. PATENT DOCUMENTS 2,257,141  9/1941  Waugh ................................. 30/339
4,404,747  9/1983  Collins ............................. 30/339 X

FOREIGN PATENT DOCUMENTS

397655  8/1933  United Kingdom ................... 30/339

Primary Examiner—Michael H. Thaler
Attorney, Agent, or Firm—John L. Voellmicke

[57] ABSTRACT

A handle for removably holding a substantially planar surgical blade having a slot therein comprises a rearward end to be held by the user and a forward end. An elongate tang at the forward end includes a proximal end, a distal end and a boss projecting outwardly from a side of the tang adjacent to the distal end thereof. This tang includes a pair of opposed longitudinal grooves extending from the distal end to the proximal end of the tang wherein the grooves run substantially along the interface of the tang and the boss. The tang also includes a relief recess projecting into the boss to a depth at least as deep as that portion of the boss extending outwardly from the grooves. The recess divides the boss into a forward boss portion and a rearward boss portion.

13 Claims, 6 Drawing Figures

SURGICAL BLADE HANDLE

BACKGROUND OF THE INVENTION

1. Field of the Invention

The present invention relates to a surgical blade handle and more particularly concerns an improved surgical blade handle that provides for easier attachment of the surgical blade thereto.

2. Description of the Prior Art

Surgical blade handles which allow removable attachment of disposable surgical blades are used in numerous surgical procedures. These handles provide the advantage of allowing the surgeon to choose the exact type of blade required for each surgical procedure and, if necessary, to change blades during a surgical procedure. The blades are relatively inexpensive compared to the cost of the handles so that a new sharp blade can be used for each surgical procedure and discarded after that use.

Known surgical blades are made from sheet steel and have a sharp cutting edge and a longitudinal slot therein for cooperating with structure on the handle to allow the removable attachment of the blade to the handle. The longitudinal slot in known blades includes a narrow distal portion and a wide proximal portion. Known handles have a tang portion projecting outwardly from a distal end of the gripping portion of the handle. The tang typically has a raised portion on its side and two opposed longitudinal grooves originating at the distal tip of the tang and running along the tang approximately along the intersection of the raised portion and the tang. Known surgical blades and reusable handles are described, for example, in U.S. Pat. Nos. 1,287,411 to Parker, 1,639,996 to Groff and 3,256,874 to DeMarco.

A disadvantage of these known handles can be observed while attaching a known blade to the handle. Specifically, once the narrow portion of the blade slot engages the grooves in the handle tang the blade is bent, with the portion of the blade near the narrow portion of the slot being aligned with the grooves and the end of the wide portion of the slot riding on the top surface of the raised portion. The blade must be forced along the grooves until the full length of the narrow portion of the blade slot engages the grooves and the portion of the blade containing the wide portion of the slot snaps over the end of the raised portion of the tang. During this forcing engagement procedure, there is a risk that the user may be injured if the hand held blade slips. A similar risk of injury is also present during blade removal. Injury can be significant since the blade is designed to efficiently cut human flesh. Even if an instrument, such as forceps, is used to hold the blade there is still a chance of damaging the presently known blade or of accidental dropping of the blade and/or handle or of accidental cutting. Also, if the blade slips within the forceps, there is the potential for generating metal particles that could be deposited in the surgical patient.

U.S. Pat. No. 4,123,840 to Rumer, Jr. teaches a surgical blade package, with a pouch design, which allows the user to install a blade on a handle by grasping the exterior of the pouch, which contains the blade, and forcing the handle tang into the pouch. It is apparent that high attachment forces could possibly cause the smooth sharp surgical blade to slice through the pouch material and injure the user.

Although the prior art addresses reusable handles that provide structure for the removable attachment of surgical blades there is still a need for a simple, straightforward, easily fabricated surgical blade handle which offers lower assembly forces and reduced potential for accidental cutting and blade damage.

SUMMARY OF THE INVENTION

The handle of the present invention for removably holding a substantially planar surgical blade having a slot therein comprises a rearward end to be held by the user and a forward end. An elongate tang at the forward end includes a proximal end, a distal end and a boss projecting outwardly from a side of the tang adjacent to the distal end of the tang. The tang also includes a pair of opposed longitudinal grooves extending from the distal end to the proximal end of the tang. These grooves run substantially along the interface of the tang and the boss. The tang also includes a relief recess projecting into the boss to a depth at least as deep as that portion of the boss extending outwardly from the grooves wherein the recess divides the boss into a forward boss portion and a rearward boss portion.

In accordance with the preferred embodiment of the present invention, a rigid oblong handle for removably holding a substantially planar blade having a slot with a relatively wide proximal portion, a relatively narrow distal portion and a transition portion therebetween comprises a rearward end to be held by the user and a forward end. An elongate tang, at the forward end, includes a proximal end, a distal end and an elongate boss projecting outwardly from a side of the tang adjacent to the distal end of the tang. This boss is shorter in length than the length of the slot in the surgical blade and narrower in width than the width of the wide proximal portion of the surgical blade slot. The tang further includes a pair of opposed longitudinal grooves originating at the distal end and terminating in the proximal end of the tang. These grooves run substantially along the interface of the tang and the boss. The grooves are adapted to receive the narrow distal portion of the surgical blade slot and are wider than the thickness of the surgical blade in an area adjacent to the surgical blade slot. The tang also includes a relief recess projecting into the boss to a depth at least as deep as that portion of the boss extending outwardly from the grooves, the recess thereby dividing the boss into a forward boss portion and a rearward boss portion. This relief recess is positioned so that the distance between the distal end of the forward boss portion and the distal end of the rearward boss portion is less than the length of the narrow distal portion of the surgical blade slot.

A number of advantages and objectives are attained consistent with the priciples of the present invention. Primarily, the present invention provides a simple, straightforward, easily fabricated surgical blade handle which offers lower assembly forces and reduces potential for accidental cutting or slicing of the user's fingers during blade engagement and removal. Also, the present invention reduces the potential for blade damage when the blade is mechanically retained, e.g., using forceps, during engagement and removal.

DETAILED DESCRIPTION

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Figures 1, 2, 3:
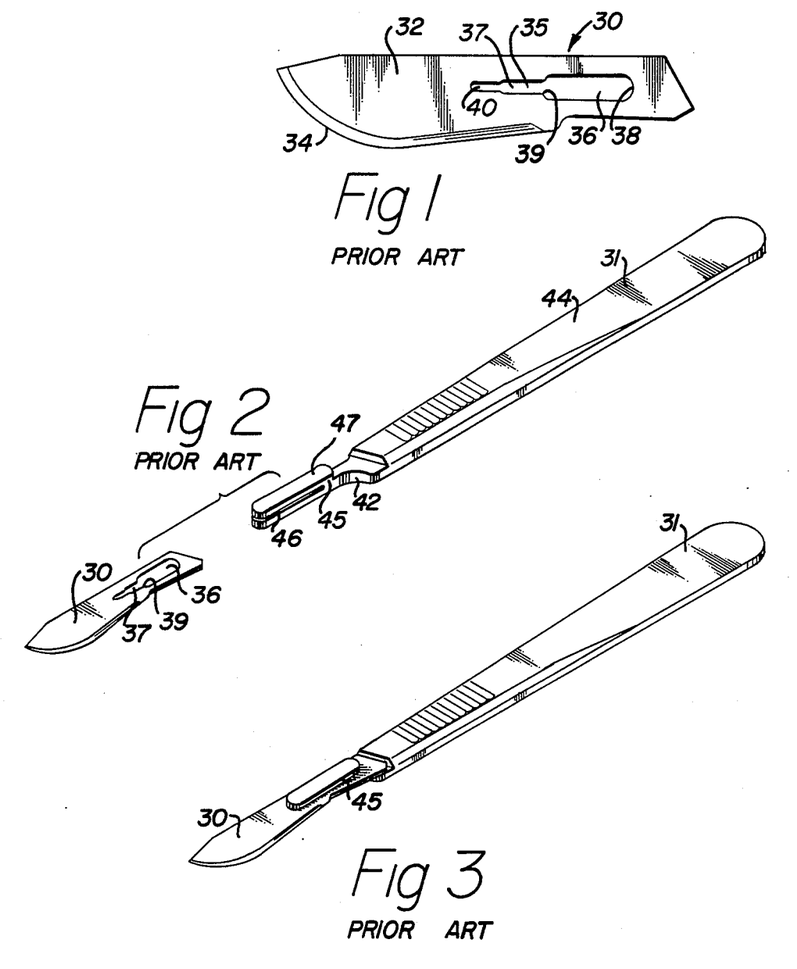
FIG. 1 is a side elevation view of a known disposable surgical blade.
FIG. 2 is a perspective view of a known surgical blade handle illustrated with the known surgical blade of FIG. 1.
FIG. 3 is a perspective view of a known surgical blade engaged with a known surgical blade handle.
Figures 4, 5:
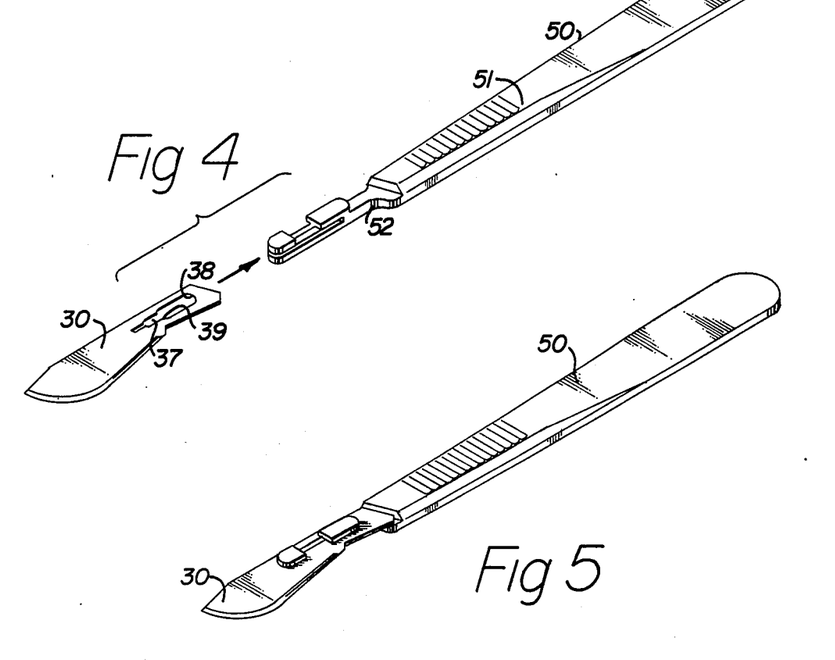
FIG. 4 is a perspective view of the preferred surgical blade handle of the present invention and a surgical blade.
FIG. 5 is a perspective view of the preferred surgical blade handle shown with the surgical blade engaged thereon.
Figure 6:
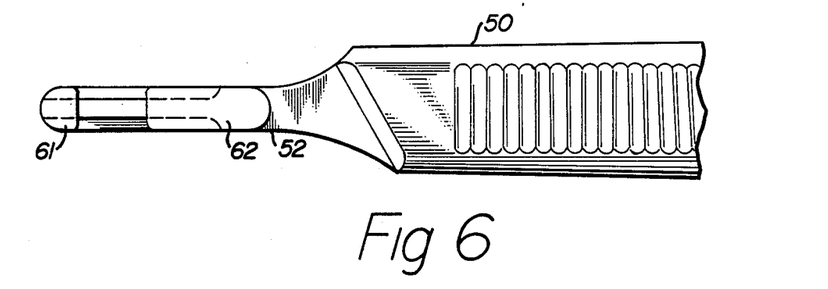
FIG. 6 is a top plan view of the forward end of the preferred surgical blade handle.
Figure 7:
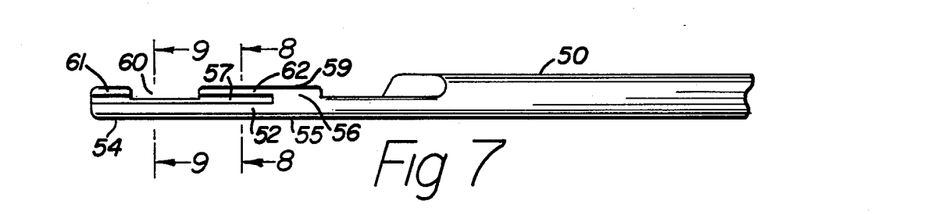
FIG. 7 is a side elevation view of the forward end of the preferred surgical blade handle.
Figure 8:
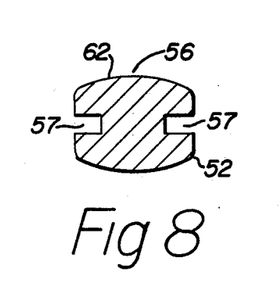
FIG. 8 is a cross-sectional view of the handle of FIG. 7 taken along the line 8—8.
Figure 9:
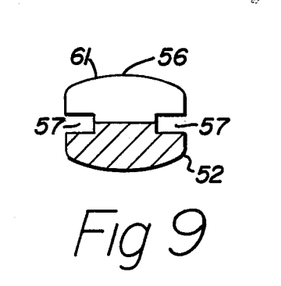
FIG. 9 is a cross-sectional view of the handle of FIG. 7 taken along line 9—9.

FIGS. 1-3 depict a typical known disposable surgical blade 30 and a known reusable handle 31. Known blades typically include an oblong planar body 32 made of stainless steel with a sharp cutting edge 34 and an engagement slot 35 for cooperating with structure on the handle to allow removable attachment of the blade to the handle. This engagement slot includes a relatively wide proximal portion 36, a relatively narrow distal portion 37 and a transition portion 39 separating the wide and narrow portions. The distal end of portion 37 is narrower than the remainder of portion 37 to form an area 40 where the distance across the slot is usually controlled to a closer dimensional tolerance to improve the fit between the blade and the handle.

Known handle 31 includes tang portion 42 projecting outwardly from the gripping portion 44 of the handle. The tang portion has a raised portion 45 on its side, a top surface 47 of the raised portion and two opposed longitudinal grooves 46 running along the tang approximately at the intersection of the raised portion and the tang. Grooves 46 are sized and spaced to accept narrow distal portion 37 of the blade slot. Blade 30 is attached to handle 31 by holding the distal end of the blade in one hand and the gripping portion of the handle in the other hand and moving the blade toward the tang so that the grooved portion of the tang engages transition portion 39 and then narrow distal portion 37 of the blade slot while a proximal end 38 of the blade slot rests on the top surface 47 of raised portion 45. As the narrow distal portion of the blade slot becomes more engaged with the tang grooves, that portion of the blade adjacent to narrow distal portion 37 is forced into alignment with the grooves, bending the blade, so that proximal end 38 of the blade slot presses against top surface 47 causing a frictional resistance to blade engagement. This frictional resistance continues until the narrow distal portion of the blade slot is fully engaged with the tang grooves and the proximal end of the blade slot snaps over the proximal end of raised portion 45 and the blade is locked in place, as best illustrated in FIG. 3.

Adverting to FIGS. 4-9, wherein the present invention is illustrated, a preferred surgical blade handle 50, for removably holding disposable surgical blade 30, includes a substantially planar rearward end 51 to be held by the user and a tang 52 having a distal end 54 and a proximal end 55. An elongate boss 56, having top surface 59, projects outwardly from a side of the tang adjacent to the distal end of the tang. The boss is preferably shorter in length than the length of slot 35 of the surgical blade and narrower in width than wide proximal portion 36 of the blade slot.

A pair of longitudinal grooves 57 originates at distal end 54 and terminates in proximal end 55 of the tang. Longitudinal grooves 57 run along the tang approximately at the intersection of the boss and the tang. The grooves are wider than the thickness of surgical blade 30 in an area adjacent to the surgical blade slot and are adapted to receive narrow distal portion 37 of the surgical blade slot.

Tang 52 includes a relief recess 60 projecting into boss 56 to a depth at least as deep as that portion of the boss extending outwardly from the longitudinal grooves. Recess 60 divides the boss into a forward boss portion 61 and a rearward boss portion 62. The recess is preferably positioned so that the distance between the distal end of forward boss portion 61 and the distal end of rearward boss portion 62 is less than the length of narrow portion 37 of the blade slot so that when the blade is engaged with the handle, part of the narrow portion 37 of the slot will be contained by that portion of the longitudinal grooves within the rearward boss portion. Also, in this preferred embodiment, the recess is longer than the forward boss portion when measured long the longitudinal axis of the boss.

Figure 10:
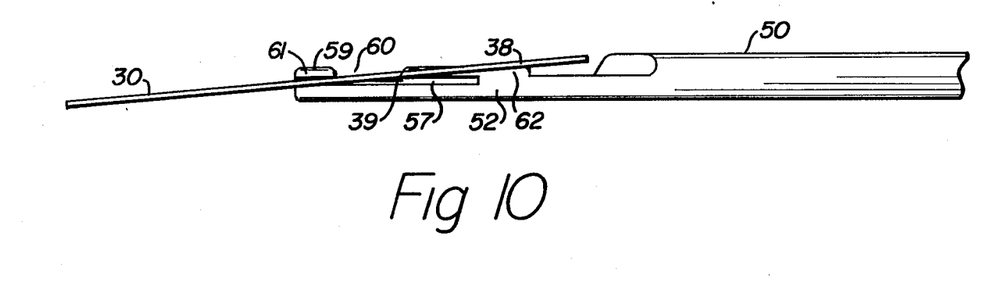
FIGS. 10-13 are side elevation views illustrating the sequential steps of engaging the blade with the preferred surgical blade handle.

Referring now to FIGS. 10-13, taken together with FIG. 1, blade 30 is attached to handle 50 by holding the distal end of the blade in one hand and the rearward end of the handle in the other hand and advancing the blade toward the tang so that the grooved portion of the tang, at forward boss portion 61, engages transition portion 39 and then narrow distal portion 37 of the blade slot. Unlike the known handle, hereinabove described, the blade, when using preferred handle 50, does not immediately bend because the portion of the top surface of the boss which could engage the blade at proximal end 38 is removed by virtue of the presence of relief recess 60. This is an important feature of the present invention because tang 52 of handle 50 allows blade 30 to be substantially engaged thereon before there is any forced bending of the blade, as best illustrated in FIG. 10.

Figure 11:
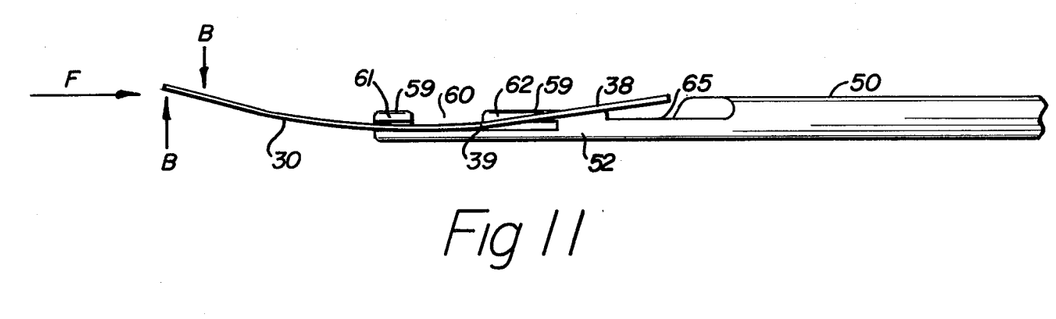
Figure 12:
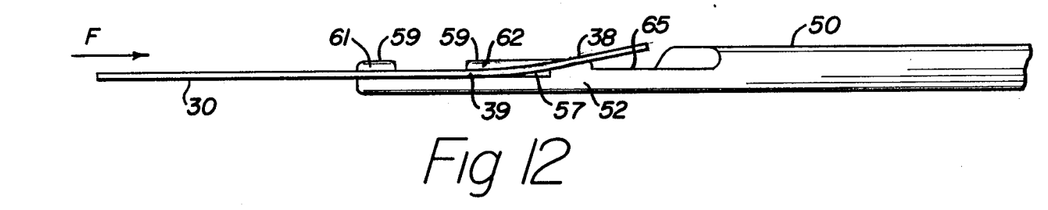
Figure 13:
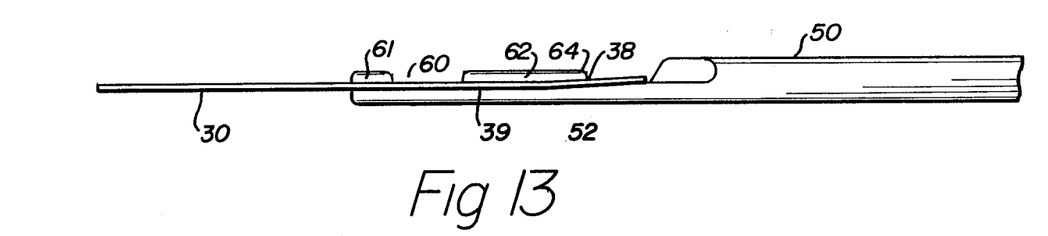

During that portion of the engagement procedure where forced bending has been eliminated, frictional resistance to engagement and the corresponding potential for user injury is also substantially reduced. Here, as illustrated in FIG. 10, transition portion 39 of the blade slot is adjacent to the distal end of rearward boss portion 62 and proximal end 38 of slot 35 is resting on top surface 59 of the boss, a short distance from the proximal end of the boss. At this point in the engagement procedure, transition portion 39 of the blade slot must be guided into longitudinal grooves 57 within rearward boss portion 62. As best illustrated in FIG. 11, this is accomplished by applying a bending force B to the distal end of the blade to align transition portion 39 with the longitudinal grooves and applying a longitudinal force F to slide the transition portion into the grooves. At this point, as illustrated in FIG. 12, the blade is almost completely engaged with the tang and proximal end 38 of the blade slot is almost at the proximal end of rearward boss portion 62. Additional force F along the longitudinal axis of the blade will cause the blade to move along longitudinal grooves 57 until proximal end 38 of the blade slot snaps over the proximal portion of rearward boss portion 62 and the blade is locked in place, as illustrated in FIG. 13. If proximal end 38 of the blade slot is close to the proximal end of rearward boss portion 62 when the transition portion enters the longitudinal grooves of the rearward boss portion, the steps of engagement shown in FIGS. 11–13 can be accomplished by a smooth bending and forcing motion which will cause the blade to pass quickly from the position illustrated in FIG. 11 to the position illustrated in Fig. 13. A large radius 64 may be included on the proximal end of rearward boss portion 62 to help reduce engagement forces.

There is a practical limit as to how far the relief recess can be positioned from the distal tip of the tang. The most rearward position of the relief recess should preferably still allow a portion of the longitudinal grooves in the rearward boss portion to engage a portion of narrow distal portion 37 of the blade slot when the blade is fully installed so that the blade is prevented from moving in a direction perpendicular to the longitudinal grooves by portions of the grooves in both the forward boss portion and the rearward boss portion. If only the grooves in the forward boss portion engage narrow distal portion 37, then the blade will be less stably and firmly held by the tang. A known surgical blade, similar to the surgical blade of FIG. 1, manufactured by the Bard-Parker Division of Becton, Dickinson and Company, Lincoln Park, N.J., has a narrow distal slot portion which is approximately 7.2 mm long. To accommodate this blade it is preferred, but not necessary, that the combined length of the forward boss portion and the relief recess measured along the grooves be within the range of about 5.5 to 6.5 mm.

It should be noted that blade contact surface 65 is not aligned with grooves 57 but is slightly angled so that when the blade is installed, as illustrated in FIG. 13, the proximal end of the blade is biased in a direction toward the top surface of the boss. This biasing or bending of the blade provides a tighter fit by forcing the blade against the sides of the grooves.

Removal of the blade from the preferred handle is accomplished by pushing the proximal end of the blade away from contact surface 65, so that proximal end 38 of the blade slot clears top surface 59 of rearward boss portion 62 while simultaneously pulling the blade away from the handle tang portion.

Figure 14:
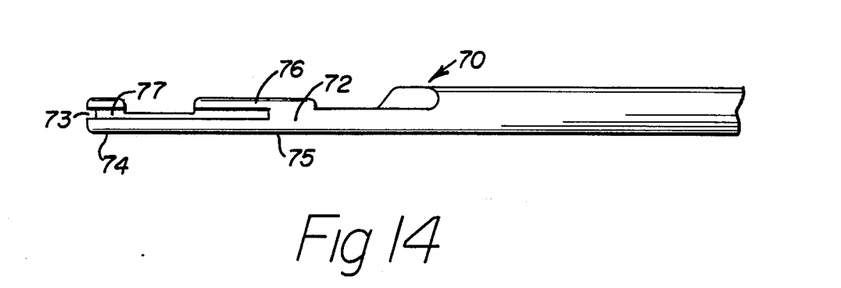
FIG. 14 is a side elevation view of the forward end of an alternative embodiment of the surgical blade handle.

Turning now to FIG. 14, viewed in connection with FIG. 1, an alternative embodiment of the present surgical blade handle 70 includes a tang 72 having a distal portion 74 and a proximal portion 75. An elongate boss 76 projects outwardly from a side of the tang adjacent to the distal end of the tang. A pair of longitudinal grooves 77 originates at distal end 74 and terminates in proximal end 75. A third groove 73 runs across the distal end of the tang joining with grooves 77. All grooves run along the outside of the tang approximately at the intersection of the boss and the tang. The grooves are wider than the thickness of surgical blade 30 in an area adjacent to the surgical blade slot and are adapted to receive narrow distal portion 37 of the surgical blade slot. Third groove 73 provides additional surfaces for supporting the blade 30 against forces which are perpendicular to the planar body of the blade. In this embodiment, boss 76 may be longer than length of slot 35 in the surgical blade, but not longer than the length of slot 35 plus the depth of groove 73 measured along the longitudinal axis of the tang.

Figure 15:
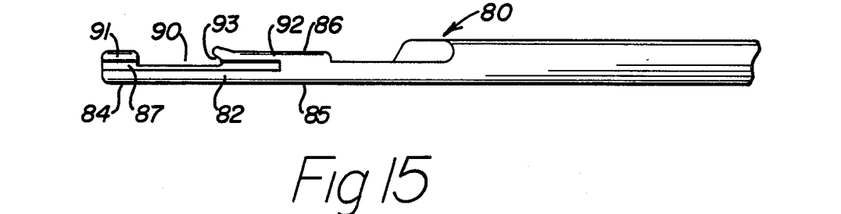
FIG. 15 is a side elevation view of the forward end of another alternative embodiment of the surgical blade handle.
Figure 16:
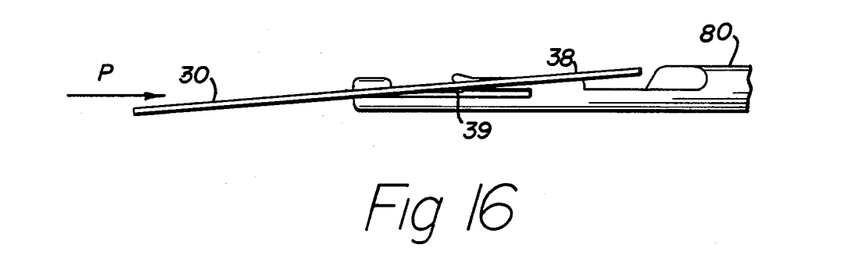
FIG. 16 is a side elevation view of the forward end of the handle of FIG. 15 shown with a surgical blade partially engaged thereon.

Adverting now to FIGS. 15 and 16, taken together with FIG. 1, another alternative embodiment of the present surgical blade handle 80 includes a tang 82 having a distal end 84 and an proximal end 85. An elongate boss 86 projects outwardly from a side of the tang adjacent to the distal end of the tang. A pair of longitudinal grooves 87 originates at distal end 84 and terminates in proximal end 85. Longitudinal grooves 87 run along the tang approximately at the intersection of the boss and the tang. The grooves are wider than the thickness of surgical blade 30 in an area adjacent to the surgical blade slot and are adapted to receive narrow distal portion 37 of the surgical blade slot.

Tang 82 includes a relief recess 90 projecting into boss 86 to a depth at least as deep as that portion of the boss extending outwardly from the longitudinal grooves. Recess 90 divides the boss into a forward boss portion 91 and a rearward boss portion 92. The recess is preferably positioned so that the distance between the distal end of forward boss portion 91 and the distal end of rearward boss portion 92, measured along grooves 87, is less than the length of narrow portion 37 of the blade slot so that when the blade is engaged with the handle, part of the narrow portion 37 of the slot will be contained by that portion of the longitudinal grooves within the rearward boss portion. The distal end of rearward boss portion 92 includes a substantially smooth cam surface 93 inclined toward the distal end of the tang so that the recess is longest when measured in a longitudinal direction at the base of the recess. The cam surface is shaped to facilitate attachment of blade 30 to handle 80 at the step in the attachment procedures where transition portion 39 of the surgical blade is adjacent to the distal end of rearward boss portion 92, which in this embodiment is cam surface 93. Instead of applying a bending force to the distal end of the blade to align transition portion 39 with the longitudinal grooves in the rearward boss portion and then applying a longitudinal force to slide the transition portion along the grooves, all that is necessary is to provide a longitudinal force P, since cam surface 93 will guide the transition portion of the blade slot toward and into the grooves. Continued application of force P along the longitudinal axis of the blade will cause the blade to move along the longitudinal grooves until proximal end 38 of the blade slot snaps over the proximal portion of the boss and the blade is locked in place (not shown).

A wide variety of rigid materials are suitable for fabricating the surgical blade handle of the present invention. However, metal alloys are preferred due to their inherent rigidity and ability to withstand repeated blade installations and removals. In particular, alloys exhibiting good corrosion resistance or alloys that can be plated with corrosion resistant metals are desirable, with a forging quality copper alloy comprising about 69-73% copper, 9-11% nickel and the remainder in zinc being preferred. In addition, because the surgical blade handle of the present invention provides lower blade installation forces, plastic materials such as, but not limited to, ABS and reinforced polypropylene may be used. It is anticipated that plastic handles will have a shorter life span and will exhibit less rigidity. However, the cost of fabricating plastic handles is also less than metal handles. In many surgical procedures it is preferred that the surgical blade handle should be sterile when used. Accordingly, materials should be selected for compatability with the sterilization processes to which the surgical blade handle will be exposed.

Thus, it can be seen that the present invention provides a simple, straightforward, easily fabricated surgical blade handle which offers lower assembly forces and reduces potential for accidental cutting or slicing of the user's fingers during blade engagement and removal. Also, the present invention reduces potential for blade damage when the blade is engaged or removed from the handle using mechanical means such as forceps.

What is claimed is:

1. A handle and surgical blade assembly wherein the surgical blade is removably engaged with the handle comprising: a substantially planar surgical blade having a slot with a relatively wide proximal portion and a relatively narrow distal portion and a transition portion therebetween;
   a handle including a rearward end to be held by the user and a forward end;
   an elongate tang at said forward end having a proximal end, a distal end and an elongate boss projecting outwardly from a side of said tang adjacent to said distal end, said boss being narrower in width than the width of said wide proximal portion of said surgical blade slot;
   said tang including a pair of opposed longitudinal grooves originating at said distal end and terminating in said proximal end, said grooves running substantially along the interface of said tang and said boss, said grooves being wider than the thickness of said surgical blade in an area adjacent to said surgical blade slot, said grooves adapted to receive the narrow distal portion of said surgical blade slot;
   said tang including a relief recess projecting into said boss to a depth at least as deep as that portion of said boss extending outwardly from said grooves away from said tang, said recess thereby dividing said boss into a forward boss portion and a rearward boss portion, said recess being positioned so that the distance between the distal end of said forward boss portion and the distal end of said rearward boss portion is less than the length of said narrow distal portion of said surgical blade slot; and
   said surgical blade being engaged with said handle so that said narrow distal portion of said slot is engaged by said forward boss portion and said rearward boss portion and also is engaged in said longitudinal grooves and said boss is protruding through said slot.

2. The handle and surgical blade assembly of claim 1 wherein the length of said boss is shorter than the length of said slot in said surgical blade.

3. The handle and surgical blade assembly of claim 1 wherein said recess is longer than said forward boss portion when measured along the longitudinal axis of said boss.

4. The handle and surgical blade assembly of claim 1 wherein the combined length of said forward boss portion and said relief recess measured along said grooves is within the range of about 5.5 to 6.5 mm.

5. The handle and surgical blade assembly of claim 1 wherein said rearward end is substantially planar.

6. The handle and surgical blade assembly of claim 1 wherein said handle is made of plastic.

7. The handle and surgical blade assembly of claim 1 wherein said handle is made of metal.

8. The handle and surgical blade assembly of claim 7 wherein said metal is an alloy including copper, nickel and zinc.

9. A handle for removably holding a substantially planar surgical blade having a slot with a relatively wide proximal portion and a relatively narrow distal portion and a transition portion therebetween comprising:
   a rearward end to be held by the user and a forward end;
   an elongate tang at said forward end having a proximal end, a distal end and an elongate boss projecting outwardly from a side of said tang adjacent to said distal end, said boss being narrower in width than the width of the wide proximal portion of the surgical blade slot;
   said tang including a pair of opposed longitudinal grooves originating at said distal end and terminating in said proximal end, said grooves running substantially along the interface of said tang and said boss, said grooves being wider than the thickness of the surgical blade in an area adjacent to the surgical blade slot, said grooves adapted to receive the narrow distal portion of the surgical blade slot;
   said tang including a relief recess projecting into said boss to a depth at least as deep as that portion of said boss extending outwardly from said grooves away from said tang, said recess thereby dividing said boss into a forward boss portion and a rearward boss portion, said recess being positioned so that the distance between the distal end of said forward boss portion and the distal end of said rearward boss portion is less than the length of the narrow distal portion of the surgical blade slot; and
   the distal end of said rearward boss portion including a substantially smooth cam surface inclined toward the distal end of said tang so that said recess is longest when measured in a longitudinal direction at the base of said recess, said cam surface being shaped so that insertion of said tang into the blade slot, wherein said grooves engage the narrow distal portion of the blade slot, and moving the blade longitudinally toward said rearward end of said handle causes the transition portion of the blade slot to engage said cam surface guiding the transition portion toward and into said grooves.

10. A rigid handle for removably holding a substantially planar surgical blade having a slot with a relatively wide proximal portion, a relatively narrow distal portion and a transition portion therebetween comprising:

a rearward end to be held by the user and a forward end;

an elongate tang at said forward end having a proximal end, a distal end and an elongate boss projecting outwardly from a side of said tang adjacent to said distal end, said boss being shorter in length than the length of the slot in the surgical blade and narrower in width than the width of the wide proximal portion of the surgical blade slot;

said tang including a pair of opposed longitudinal grooves originating at said distal end and terminating in said proximal end, said grooves running substantially along the interface of said tang and said boss, said grooves being wider than the thickness of the surgical blade in an area adjacent to the surgical blade slot, said grooves adapted to receive the narrow distal portion of the surgical blade slot;

said tang including a relief recess projecting into said boss to a depth at least as deep as that portion of said boss extending outwardly from said grooves, said recess thereby dividing said boss into a forward boss portion and a rearward boss portion; and the distal end of said rearward boss portion including a substantially smooth cam surface inclined toward the distal end of said tang so that said recess is longest when measured in a longitudinal direction at the base of said recess, said cam surface being shaped so that insertion of said tang into the blade slot, wherein said grooves engage the narrow distal portion of the blade slot, and moving the blade longitudinally toward said rearward end of said handle causes the transition portion of the blade slot to engage said cam surface guiding the transition portion toward and into said grooves.

11. A handle and surgical blade assembly wherein the surgical blade is removably engaged with the handle comprising:

a substantially planar surgical blade having a longitudinal slot including a relatively wide proximal portion, a relatively narrow distal portion and a transition portion therebetween;

a handle including a rearward end to be held by the user and a forward end;

an elongate tang at said forward end having a proximal end, a distal end and an elongate boss projecting outwardly from a side of said tang adjacent to said distal end, said boss being shorter in length than the length of said longitudinal slot and narrower in width than the width of said wide proximal portion of said longitudinal slot;

said tang including a pair of opposed longitudinal grooves originating at said distal end and terminating in said proximal end, said grooves running substantially along the interface of said tang and said boss, said grooves being wider than the thickness of said surgical blade in an area adjacent to said longitudinal slot, said grooves adapted to retain said narrow distal portion of said longitudinal slot;

said tang including a relief recess projecting into said boss to a depth at least as deep as that portion of said boss extending outwardly from said grooves away from said tang, said recess thereby dividing said boss into a forward boss portion and a rearward boss portion;

said relief recess being positioned so that the distance between the distal end of said forward boss portion and the distal end of said rearward boss portion is less than the length of said narrow distal portion of said longitudinal slot; and said surgical blade being engaged with said handle so that said narrow distal portion of said longitudinal slot is engaged in said longitudinal grooves and said boss is protruding through the full length of said longitudinal slot.

12. The handle and surgical blade assembly of claim 11 wherein said recess is longer than said forward boss portion when measured along the longitudinal axis of said boss.

13. The handle and surgical blade assembly of claim 11 wherein the combined length of said forward boss portion and said relief recess measured along said grooves is within the range of about 5.5 to 6.5 mm.

* * * * *